(12) United States Patent
Bouch et al.

(10) Patent No.: US 12,312,598 B2
(45) Date of Patent: May 27, 2025

(54) METHOD OF GENERATING HEMANGIOBLASTS

(71) Applicant: The Hospital for Sick Children, Toronto (CA)

(72) Inventors: Sheena Bouch, Toronto (CA); Michael Litvack, Toronto (CA); Martin Post, Toronto (CA)

(73) Assignee: The Hospital for Sick Children, Toronto (CA)

( * ) Notice: Subject to any disclaimer, the term of this patent is extended or adjusted under 35 U.S.C. 154(b) by 844 days.

(21) Appl. No.: 17/598,593

(22) PCT Filed: Mar. 27, 2020

(86) PCT No.: PCT/CA2020/050406
§ 371 (c)(1),
(2) Date: Sep. 27, 2021

(87) PCT Pub. No.: WO2020/191500
PCT Pub. Date: Oct. 1, 2020

(65) Prior Publication Data
US 2022/0162556 A1 May 26, 2022

Related U.S. Application Data

(60) Provisional application No. 62/825,352, filed on Mar. 28, 2019.

(51) Int. Cl.
| | | |
|---|---|---|
| *C12N 5/0789* | (2010.01) | |
| *A61K 35/15* | (2025.01) | |
| *C12N 5/071* | (2010.01) | |
| *C12N 5/0786* | (2010.01) | |

(52) U.S. Cl.
CPC ......... *C12N 5/0647* (2013.01); *C12N 5/0645* (2013.01); *C12N 5/0692* (2013.01); *A61K 35/15* (2013.01); *C12N 2500/02* (2013.01); *C12N 2500/90* (2013.01); *C12N 2501/125* (2013.01); *C12N 2501/155* (2013.01); *C12N 2501/165* (2013.01); *C12N 2501/22* (2013.01); *C12N 2501/2303* (2013.01); *C12N 2501/727* (2013.01); *C12N 2506/03* (2013.01); *C12N 2506/45* (2013.01)

(58) Field of Classification Search
CPC .. C12N 5/0647; C12N 5/0645; C12N 5/0692; C12N 2500/02; C12N 2500/90; C12N 2501/125; C12N 2501/155; C12N 2501/165; C12N 2501/22; C12N 2501/2303; C12N 2501/727; C12N 2506/03; C12N 2506/45; A61K 35/15
See application file for complete search history.

(56) References Cited

U.S. PATENT DOCUMENTS

| | | | |
|---|---|---|---|
| 9,745,553 B2 | 8/2017 | Keller et al. | |
| 9,834,754 B2 | 12/2017 | Keller et al. | |
| 9,994,821 B2 | 6/2018 | Keller et al. | |
| 2009/0017539 A1 | 1/2009 | Spanholtz | |
| 2011/0086424 A1* | 4/2011 | Lanza | C12N 5/0647 |
| | | | 435/325 |
| 2013/0230921 A1 | 9/2013 | Keller et al. | |
| 2014/0322808 A1 | 10/2014 | Keller et al. | |
| 2017/0335282 A1 | 11/2017 | Post et al. | |

FOREIGN PATENT DOCUMENTS

| | | |
|---|---|---|
| EP | 2647698 | 10/2013 |
| WO | 2009/104825 | 8/2009 |
| WO | 2009/137629 | 11/2009 |
| WO | 2014/012933 | 1/2014 |
| WO | 2016/127259 | 8/2016 |
| WO | 2017/097876 | 6/2017 |
| WO | 2018/209447 | 11/2018 |

OTHER PUBLICATIONS

Liao, J. K., et al., "Rho kinase (ROCK) inhibitors," J Cardiovasc Pharmacol 50(1):17-24. doi: 10.1097/FJC.0b013e318070d1bd. (Year: 2007).*
Shultz et al.—"A Lineage of Myeloid Cells Independent of Myb and Hematopoietic Stem Cells", Science Apr. 6, 2021 (Apr. 6, 2012), vol. 336, No. 6077, pp. 86-90, ISSN: 0033-8075.
Nakata et al.—"Granulocyte-macrophage colony-stimulating factor promotes the proliferation of human alveolar macrophages in vitro", The Journal of Immunology, vol. 147, 1266-1272, No. 4, Aug. 15, 1991.
Soucie et al.—"Lineage specific enhancers activate self-renewal genes in macrophages and embryonic stem cells", Science, Feb. 12, 2016, vol. 351, No. 6274.
Imperatore et al.—"SIRTI regulates macrophage self-renewal", The EMBRO Journal, 2017, vol. 36, No. 16, p. 2353-2372.
Busch et al.—"Isolation and Long-term Cultivation of Mouse Alveolar Macrophages", Bio Protoc, Jul. 20, 2019, vol. 9, No. 14, e3302.

(Continued)

*Primary Examiner* — Tracy Vivlemore
*Assistant Examiner* — Eric J Rogers
(74) *Attorney, Agent, or Firm* — Gowling WLG (Canada) LLP

(57) ABSTRACT

A method of differentiating pluripotent stem cells into hemangioblasts comprising incubating the pluripotent stem cells in a first serum-free differentiation medium comprising bone morphogenetic protein 4 (BMP4), vascular endothelial growth factor (VEGF) and stem cell factor (SCF) to induce differentiation of the pluripotent stem cells into hemangioblasts or hemangioblast-containing embryoid bodies is provided. The hemangioblasts or embryoid bodies may be cultured in a second differentiation medium comprising at least granulocyte-macrophage colony stimulating factor (GM-CSF), macrophage colony stimulating factor (M-CSF) and interleukin-3 (IL-3) for a period of time sufficient to generate alveolar-like macrophages.

14 Claims, 9 Drawing Sheets

(56) References Cited

OTHER PUBLICATIONS

Haideri et al.—"Injection of embryonic stem cell derived macrophages ameliorates fibrosis in a murine model of liver injury", Nature Partner Journals, Regenerative Medicine (2017).
Sica et al.—"Macrophages polarization in pathology", Cell. Mol. Life Sci (2-15) 72:4111-4126.
George et al.—"Macrophage polarization in Living Biology and Diseases", Intech 2014.
Burke—"Macrophages as novel cellular vehicles for gene therapy", Literature Review in Expert Opinion on Biological Therapy 3(6): 919-24 Oct. 2003.
Gomez Perdiguero et al.—"Development and Homeostasis of "Resident" Myeloid Cells: the case of the Microglia", GLIZ 61:112-120, 2012 Wiley Periodials.
Gomez Perdiguero et al.—"Myb-Independent Macrophages: A Family of Cells that Develops with Their Tissue of Residence and is involved in it Homeostasis", Cold Spring Harbor Symposia on Quantitative Biology, vol. LXXII.
Extended European Search Report—Nov. 16, 2022 EP 20776458.0.
International Search Report—PCT/CA2020/050406 dated Jun. 5, 2020.
International Search Report—PCT/CA2016/050128 dated Apr. 26, 2021.
Suzuki et al.—"Pulmonary Macrophage Transplation", Nature Oct. 23, 2014 (Oct. 23, 2014) vol. 574, No. 7523 pp. 450-454 ISSN:0028-0836.
Happle et al.—"Pulmonary transplation of macrophage progenitors as effective and long-lasting therapy for hereditary pulmonary alveolar proteinosis", Science Translation Medicine Aug. 20, 2014 (Aug. 20, 2014), vol. 6, No. 250, p. 25 Oral 113, ISSN: 1946-6234.
Suzuki et al.—"Use of induced pluripotent stem cells to recapitulate pulmonary alveolar proteinosis pathogenisis", American Journal of Respiratory and Critical Care Medicine, Jan. 15, 2014 (Jan. 15, 2014) vol. 189, No. 2, pp. 183-193, ISSN: 1073-449X.
Van Wilgenburg et al.—"Efficient, Long Term Production of Monocyte-Derived Macrophages from Human Pluripotent Stem Cells under Partly-Defined and Fully-Defined Conditions", Plos One, Aug. 12, 2013 (Aug. 12, 2013), vol. 8, No. 8, p. 71098 ISSN: 1932-6203.
Lu et al.—"Generation of functionalhemangioblasts from human embryonic stem cells", Nature Methods Jun. 2007 ) 06-007), vol. 4, No. 6, pp. 501-209, ISSN:1548-7091.
Gomez-Perdiguero et al.—"Tissue-resident macrophages originate from yolk-sac-derived erythro-myeloid progenitors", Nature Feb. 26, 2015 (Feb. 26, 2015) E pub, Dec. 3, 2014 (Dec. 3, 2014), vol. 518, No. 7540, pp. 547-551 ISSN:0028-0836.
Litvack et al.—"Alveolar-like stem cell-derived mybneg macrophages promote recovery and survival in airway disease", American Journal of Respiratory and Critical Care Medicine Jan. 5, 2016 (Jan. 5, 2016) First Published online as DOI:10.1164/rccm. 201509-1838C, ISSN: 1073-449X.

\* cited by examiner

METHOD OF GENERATING HEMANGIOBLASTS

TECHNICAL FIELD

Non-limiting embodiments disclosed herein generally relate to differentiation of cells, such as differentiation of pluripotent stem cells (PSCs) or cells derived therefrom, into alveolar-like macrophage cells.

BACKGROUND

In recent years, the discovery, isolation and engineering of human pluripotent stem cells such as embryonic stem cells (ESCs) and induced pluripotent stem cells (iPSCs) has significantly increased the capabilities and potential of cell culture models and their applications in regenerative medicine and disease modeling. The self-renewal capabilities of these cells and their ability to differentiate into numerous cell types makes them an ideal candidate for studying the differentiation pathway of specific cell types, especially those of fetal origin. Alveolar macrophages (AM) are known to be derived from the fetal liver, and can develop independently of the hematopoietic transcription factor, Myb; however, the exact mechanisms and differentiation pathways required for human AM development is yet to be elucidated as the study of AM development has largely been restricted to mice. AMs are of a different developmental origin than that of bone marrow-derived macrophages, and are able to reside in the lung niche for long periods of time, making them an ideal candidate for cell-based therapies compared to bone-marrow derived macrophages.

It would, thus, be desirable, to develop a method for generating alveolar macrophages in vitro in an effort to treat macrophage-related lung disease.

SUMMARY

A novel feeder-free, serum-free, and thus, xeno-free in vitro protocol for the differentiation of human ESCs and iPSCs into hemangioblasts, which may then be differentiated into non-naturally occurring alveolar-like macrophages (ALMs), has now been developed. This directed differentiation protocol produces human ESC- and iPSC-derived ALMs with a high degree of reproducibility, without requiring subpopulation isolation during the differentiation. While ALMs express cell surface markers and exhibit morphological and functional characteristics consistent with that of a primary AM, ALMs are able to proliferate in vitro unlike naturally occurring AMs and exhibit additional beneficial characteristics that distinguish them from naturally occurring AMs. Together, the simplicity and reproducibility of these differentiation protocols makes ALMs a prime candidate for future cell-based therapies due to their scalability potential unlike naturally occurring AMs.

In accordance with a first aspect disclosed herein, there is provided a method of differentiating pluripotent stem cells into hemangioblasts, said method comprising incubating the pluripotent stem cells in a first serum-free differentiation medium comprising bone morphogenetic protein 4 (BMP4), vascular endothelial growth factor (VEGF) and stem cell factor (SCF) for a period of time sufficient to induce differentiation of the pluripotent stem cells and generate hemangioblasts or hemangioblast-containing embryoid bodies.

In another aspect, a method for differentiating pluripotent stem cells into alveolar-like macrophages is provided. The method includes: i) incubating the pluripotent stem cells in a first serum-free differentiation medium comprising bone morphogenetic protein 4 (BMP4), vascular endothelial growth factor (VEGF) and stem cell factor (SCF) for a period of time sufficient to induce differentiation of the pluripotent stem cells to generate hemangioblasts or hemangioblast-containing embryoid bodies; and ii) culturing the hemangioblasts or embryoid bodies in a second serum-free differentiation medium comprising at least granulocyte-macrophage colony stimulating factor (GM-CSF), macrophage colony stimulating factor (M-CSF) and interleukin-3 (IL-3) for a period of time sufficient to generate alveolar-like macrophages.

In another aspect, in vitro-derived alveolar-like macrophages are provided which are advantageously independent of the hematopoietic transcription factor, Myb (i.e. Myb-independent) and which are uniquely able to proliferate in vitro. Myb-independent alveolar macrophages cannot otherwise readily be obtained from adult tissues in the quanitites required for cell-based therapies. In an embodiment of this aspect, the alveolar-like macrophages, or a precursor thereof such as hemangioblasts or haematopoietic progenitor cells, may be genetically modified to express a therapeutic agent.

In another aspect, a kit is provided comprising a first serum-free differentiation medium comprising bone morphogenetic protein 4 (BMP4), vascular endothelial growth factor (VEGF) and stem cell factor (SCF) to induce differentiation of pluripotent stem cells into hemangioblasts or hemangioblast-containing embryoid bodies; and a second serum-free differentiation medium comprising at least granulocyte-macrophage colony stimulating factor (GM-CSF), macrophage colony stimulating factor (M-CSF) and interleukin-3 (IL-3) to induce differentiation of hemangioblasts or hemangioblast-containing embryoid bodies into alveolar-like macrophages.

These and other aspects and features of non-limiting embodiments will become apparent to those skilled in the art upon review of the following description of specific non-limiting embodiments in conjunction with the accompanying drawings.

BRIEF DESCRIPTION OF THE FIGURES

The non-limiting embodiments will be more fully appreciated by reference to the accompanying drawings, in which.

Figure 1:
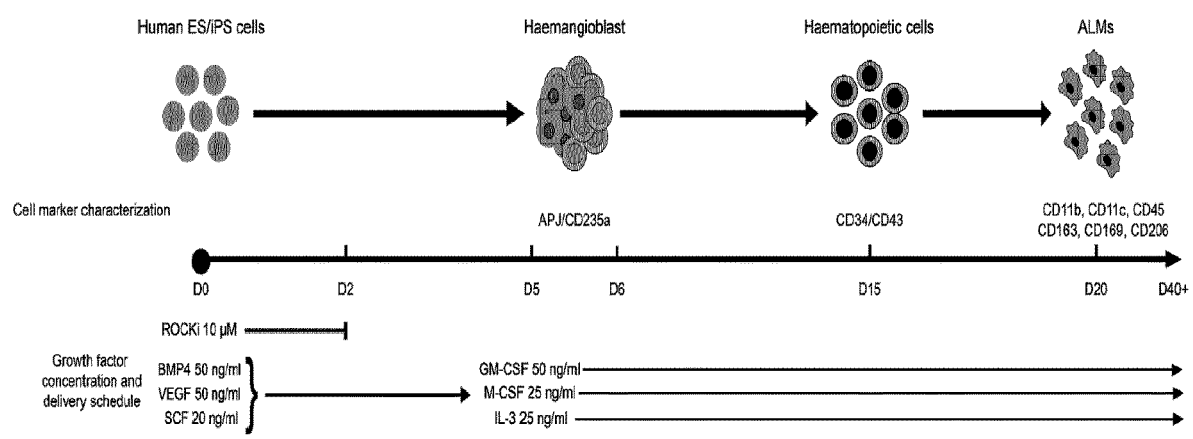
FIG. 1 is a schematic of a protocol for differentiation of alveolar-like macrophages from human ESCs and iPSCs.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION OF THE NON-LIMITING EMBODIMENT(S)

In a non-limiting embodiment, a method of differentiating pluripotent stem cells is provided. The method includes incubating the pluripotent stem cells in a first serum-free differentiation medium comprising bone morphogenetic protein 4 (BMP4), vascular endothelial growth factor (VEGF) and stem cell factor (SCF) for a period of time sufficient to induce differentiation of the pluripotent stem cells into hemangioblasts or hemangioblast-containing embryoid bodies. The hemangioblasts or hemangioblast-containing embryoid bodies may be further cultured to yield alveolar-like macrophages in a second serum-free differentiation medium comprising at least granulocyte-macrophage colony stimulating factor (GM-CSF), macrophage colony stimulating factor (M-CSF) and interleukin-3 (IL-3) for a sufficient period of time to generate non-naturally occurring alveolar-like macrophages.

As one of skill in the art will appreciate, in accordance with an embodiment, hemangioblasts or hemangioblast-containing embryoid bodies may be generated from pluripotent stem cells. For example, pluripotent stem cells (PSCs) are incubated in a first differentiation medium, preferably serum-free, sufficient to induce differentiation of the PSCs into hemangioblasts. The term "pluripotent stem cell" is used herein to refer to undifferentiated biological cells that can differentiate into specialized cells. In particular, PSCs are capable of differentiating into all three germ layers and becoming any cell type in an animal body. PSCs have a cell morphology characteristic of undifferentiated cells and form teratomas when introduced into an immunocompromised animal, such as a severe combined immunodeficiency (SCID) mouse. Teratomas typically contain cells or tissues characteristic of all three germ layers. Examples of PSCs include embryonic stem cells (ESCs), pluripotent adult stem cells and induced pluripotent stem cells (iPSCs).

Base media suitable for use in conjunction with the first differentiation medium for differentiation of PSCs into hemangioblasts may include components such as serum-free media, e.g. StemPro™-34 SFM (×1), L-ascorbic acid, L-glutamine (e.g. GlutaMAX™ supplement), penicillin/streptomycin and monothioglycerol. Such media components are generally commercially available. The cells are incubated at an appropriate temperature, e.g. 37° C., generally for a time period sufficient to yield hemangioblasts or hemangioblast-containing embryoid bodies (EBs) in which the cells are not committed to a particular germ layer, e.g. in a time period in the range of about 4-6 days, such as 5 days.

The method of differentiating PSCs into hemangioblasts or hemangioblast-containing EBs may vary with the animal origin of the stem cell, for example, human PSCs versus non-human PSCs. In one embodiment, differentiation of human PSCs into hemangioblasts or hemangioblast-containing EBs is conducted in a first differentiation medium comprising one or more growth factors such as bone morphogenetic protein 4 (BMP4), vascular endothelial growth factor (VEGF) and stem cell factor (SCF) under hypoxic conditions (e.g. 5% $O_2$), generally for a period of 1-5 days. The amounts of growth factor in the medium is generally as follows: an amount of BMP4 of no more than about 100 ng/ml, preferably in the range of about 0.1-100 ng/ml, such as 25-75 ng/ml, e.g. 50 ng/ml, an amount of VEGF of no more than about 100 ng/ml, and preferably in the range of about 0.1-100 ng/ml, such as 25-75 ng/ml, e.g. 50 ng/ml, and an amount of SCF of no more than about 50 ng/ml, and preferably in the range of about 0.5-50 ng/ml, such as 10-40, e.g. 20 ng/ml. Preferably, BMP4, VEGF and SCF corresponding with the human protein are used. The medium may also include a ROCK inhibitor in an amount in the range of 0.01-1 mM, generally for the initial differentiation period (0-2 days of the differentiation). Examples of suitable ROCK inhibitors include those that are selective for p160ROCK1, such as Y-27632 ((1R,4r)-4-((R)-1-aminoethyl)-N-(pyridin-4-yl)-cyclo-hexanecarboxamide).

In this embodiment, embryoid bodies (EBs) comprising hemangioblasts are generated, i.e. hemangioblast-containing embryoid bodies. As one of skill in the art will appreciate, differentiation of human PSCs into hemangioblasts may be confirmed based on cell expression of a hemangioblast mesoderm marker, such as c-kit, Apelin receptor/angiotensin type II receptor (APJ) and CD235a.

In a further embodiment, the method of differentiating PSCs into hemangioblast-containing EBs may be conducted in plates having microwells, e.g. 400-800 micron wells, rather than under free floating conditions. The use of microwells provides uniformity of EB size, shape and density which increases the efficiency and reproducibility of the differentiation. The number of cells plated in each microwell is generally as follows; a number of cells no more than about 1.2×10⁶ cells/microwell, and preferably, a number of cells in the range of about 1×10⁵ 1×10⁶ cells/well, such as 8×10⁵ cells/well.

In one embodiment, following the first differentiation, e.g. within about 5 days, hemangioblast-containing embryoid bodies are preferably transferred into a second differentiation medium at a density of greater than about 1:3, e.g. 1:1-1:2, for example, for the second phase of differentiation to yield hematopoietic progenitors and then alveolar-like macrophages therefrom. Preferably, single, differentiated cells emerge from the embryoid bodies during alveolar macrophage differentiation.

The hemangioblasts, e.g. in embryoid bodies, are then cultured in a second differentiation medium comprising growth factors in amounts sufficient to result in differentiation of hemangioblasts into hematopoietic progenitor cells or endothelial cells and finally alveolar-like macrophages. The medium used to differentiate hemangioblasts into hematopoietic progenitor cells and then alveolar-like macrophages is preferably serum-free and may include, but is not limited to, granulocyte-macrophage colony stimulating factor (GM-CSF), macrophage colony stimulating factor (M-CSF) and interleukin-3 (IL-3) in hematopoietic and alveolar macrophage-inducing amounts, for example, GM-CSF in an amount of no more than about 100 ng/ml, for example, in the range of about 0.1-100 ng/ml, preferably, 25 to about 75 ng/ml, such as 50 ng/ml; M-CSF in an amount of no more than about 50 ng/ml, for example, in the range of about 0.5-50 ng/ml, and preferably 15-40 ng/ml, e.g. 25 ng/ml; and IL-3 in an amount of up to about 50 ng/ml, for example in the range of about 0.5-50 ng/ml, such as 15-40 ng/ml, e.g. 25 ng/ml; for a period of time sufficient to yield alveolar-like macrophages, e.g. at least about 7 days, and generally in the range of about 7-20 days, e.g. about 10, 11, 12, 13, 14, 15, 16, 17 or 18 days.

During the second differentiation, the number of media changes was minimized to optimize differentiation efficiency. Thus, in one embodiment media is changed during the second differentiation no more than about every 4-5 days, and preferably, only half the media is changed rather than a full media change every 4-5 days. In addition, preferably, during the second differentiation, the cells were passaged at a density of greater than 1:3, e.g. 1:2 or 1:1, to optimize differentiation efficiency.

The second differentiation is generally conducted under normoxic conditions, e.g. 21% oxygen. The cells are transferred from 5% oxygen to 21% oxygen at or shortly following initiation of the second differentiation, e.g. about day 5-8 of the differentiation protocol starting from pluripotent stem cells.

In one embodiment, the hemangioblasts are cultured in the second serum-free differentiation medium for a sufficient period of time to generate alveolar-like macrophages, e.g. about 7-20 days. Differentiation is evident initially by the emergence of single cells positive for CD34 and CD43 transmembrane proteins, which indicate the emergence haematopoietic progenitors. The formation of macrophages may be confirmed, for example, when the cells assume morphology similar to that of a primary alveolar macrophage, by a determination that ALMs are able to express cell surface proteins such as CD11b, CD11c, CD45, CD163, CD169, CD206, SIRP-α, CD14, CD40, CD80, CD86, CD116, CD64, 25F9, CD68, and differentially express HLA-DR depending on the source of the ESC/iPSC. These markers have been previously reported to be expressed on primary alveolar macrophages, or that ALMs exhibit properties of alveolar macrophages such as the capacity to internalize acetylated low density lipoproteins (Ac-LDL) and foreign bodies, e.g. bacteria. Further conditioning is conducted to yield functional alveolar-like macrophages. As used herein, the term "alveolar-like macrophage" refers to non-naturally occurring macrophages, generated in vitro from hemangioblasts prepared from PSCs, and which express cell surface markers expressed by naturally occurring alveolar macrophages, including one or more of CD11b, CD11c, CD45, CD163, CD169, CD206, SIRP-α, HLA-DR, CD14, CD40, CD80, CD86, CD116, CD64, 25F9 and CD68, have a capacity for uptake of AcLDL and are able to proliferate in vitro. The formation of alveolar-like macrophages may also be confirmed based on functional characteristics, such as phagocytic activity, e.g. take up apoptotic material and bacteria. Alveolar-like macrophages resulting from the method provided herein are able to attain airway residence.

In vitro-generated alveolar-like macrophages, or one or more of their precursor cell types such as PSCs, hemangioblast-containing EBs, hemangioblasts or hematopoietic progenitors, may be genetically altered, for example using well-established biotechnological techniques, to generate alveolar-like macrophages carrying one or more genes of interest, e.g. for targeted gene correction or for targeted airway delivery of a therapeutic agent (such as a protein, cytokine or growth factor useful to treat a lung disease). Such genetically altered alveolar-like macrophages have advantageously been found to effectively express a desired therapeutic product without eliciting in an animal host an undesirable immune response. Examples of therapeutic agents that may be delivered via in vitro-generated genetically modified alveolar-like macrophages include, but are not limited to, anti-inflammatory agents such as IL-10, antimicrobial agents such as alpha- and beta-defensins or nitric oxide synthase to optimize bacterial killing, elafin (anti-elastase protein inhibitor), alpha-1 antitrypsin, agents capable of dissolving mucus, agents that stimulate vasodilation, agents that enhance phagocytosis, and agents that target cancer cells (such as lung cancer cells).

In vitro-derived alveolar-like macrophages, which may be genetically modified, according to a non-limiting embodiment may be used to treat lung disease in a mammal. The terms "treat", "treating" or "treatment" are used herein to refer to methods that favorably alter a lung disease or disorder, including those that moderate, reverse, reduce the severity of, or protect against, the progression of a lung disease or disorder. For use to treat such a disease, a therapeutically effective amount of in vitro-derived alveolar-like macrophages are administered to a mammal in need of treatment. The term "therapeutically effective amount" is an amount of alveolar-like macrophages required to treat the disease that does not exceed an amount that may cause significant adverse effects to the mammal in need of treatment. Alveolar-like macrophage dosages that are therapeutically effective will vary on many factors including the nature of the condition to be treated, the mammal being treated and the dosage form utilized for administration. Appropriate dosages for use in such a treatment include dosages sufficient to result in airway residence of administered in vitro-derived alveolar-like macrophages, and preferably, an airway residence of at least about 0.5%, preferably greater than 1-5%, and more preferably, greater than 10%, for example, at least 15-20% or greater. In one embodiment, the dosage of in vitro-derived alveolar-like macrophages useful to treat a lung disease or disorder may be a dosage in the range of about 10⁵ to 10⁸ cells, for a sufficient period of time to achieve treatment. The treatment regimen may include daily administration of alveolar-like macrophages, or dosages administered more or less frequently, e.g. on alternate days, weekly, or multiple dosages a day. The term "about" is used herein to mean an amount that may differ somewhat from the given value, by an amount that would not be expected to significantly affect activity or outcome as appreciated by one of skill in the art, for example, a variance of from 1-10% from the given value.

In one embodiment, the present alveolar-like macrophages may be used to treat various macrophage-associated lung diseases. Implantation of the alveolar-like macrophages generated by the present method provides a non-pharmacological method of regenerating alveolar tissue in the treatment of genetic diseases such as adenosine deaminase (ADA)-deficiency, cystic fibrosis, hereditary pulmonary alveolar proteinosis (herPAP), and others, as well as acquired lung diseases such as chronic obstructive pulmonary disease (COPD), acute respiratory distress syndrome (ARDS), bronchopulmonary dysplasia (BPD), pulmonary fibrosis, lung cancer, radiation induced lung injury (RILI), ventilator-induced lung injury (VILI), asthma, and bacterial or viral infections such as respiratory syncytial virus (RSV), SARS-CoV-1 and SARS-CoV-2 (nCoVID-19).

Alveolar-like macrophages in accordance with a non-limiting embodiment may be formulated for prophylactic and therapeutic use by combination with a pharmaceutically acceptable carrier. The expression "pharmaceutically acceptable" means acceptable for use in the pharmaceutical and veterinary arts, i.e. not being unacceptably toxic or otherwise unsuitable. As one of skill in the art will appreciate, the selected carrier may vary with intended mode of administration. In one embodiment, alveolar-like macrophages may be formulated for administration by infusion or injection into a mammalian airway, e.g. intra-tracheally or intranasally, and thus, are formulated as a suspension in a medical-grade, physiologically acceptable carrier, such as an aqueous solution in sterile and pyrogen-free form, optionally buffered or made isotonic. The carrier may be a carbohydrate-containing solution (e.g. dextrose), an animal-derived or synthetic surfactant, or a saline solution comprising sodium chloride and optionally buffered. Suitable saline solutions may include varying concentrations of sodium chloride, for example, normal saline (0.9%), half-normal saline (0.45%), quarter-normal saline (0.22%), and solutions comprising greater amounts of sodium chloride (e.g. 3%-7%, or greater). Saline solutions may optionally include additional components, e.g. carbohydrates such as dextrose and the like. Examples of saline solutions including additional components, include Ringer's solution, e.g. lactated or acetated Ringer's solution, phosphate buffered saline (PBS), TRIS (hydroxymethyl) aminomethane hydroxymethyl) aminomethane)-buffered saline (TBS), Hank's balanced salt solution (HBSS), Earle's balanced solution (EBSS), standard saline citrate (SSC), HEPES-buffered saline (HBS) and Gey's balanced salt solution (GBSS).

In other non-limiting embodiments, alveolar-like macrophages may be formulated for administration by routes including, but not limited to, inhalation. In this regard, aerosol formulations may be prepared in which suitable propellant adjuvants are used. Other adjuvants may also be added to the composition regardless of how it is to be administered, for example, anti-microbial agents may be added to the composition to prevent microbial growth over prolonged storage periods.

In one embodiment, the present method advantageously provides a highly efficient growth-factor defined and extracellular matrix-independent in vitro differentiation protocol for the formation of hemangioblasts derived from PSCs, which can be further differentiated to generate alveolar-like macrophages suitable for use, e.g. for in vivo administration to mammalian lungs, to replace dysfunctional alveolar macrophages and promote survival of mammals with lung disease. The present alveolar-like macrophages, while functionally similar to naturally occurring alveolar macrophages, may exhibit improved phagocytic activity, e.g. increased take up of apoptotic material and bacteria, as compared to primary alveolar macrophages (by at least about 10%) and bone marrow-derived macrophages (by at least about 2-fold), as well as the ability to be expanded in vitro for periods of time which exceed the expansion capability of primary alveolar macrophages, e.g. expansion in vitro of greater than 1 month, preferably for multiple months, e.g. 4-6 months, greater than a year, or more. In addition to functional differences, the present alveolar-like macrophages may exhibit cell surface marker characteristics that differ from primary alveolar macrophages, for example, increased expression of cell-surface protein, CD11b, e.g. exhibit at least 50% greater expression of CD11b than CD11b expression in primary alveolar macrophages.

It is noted that the present alveolar-like macrophages possess properties that render them more suitable for use in therapy than their naturally occurring counterparts. First, the present ALMs provide a homogeneous stable phenotype, providing a homogeneous population of cells, whereas naturally occurring alveolar macrophages are heterogeneous in nature, comprising a mixture of phenotypes that change in response to variations in the local environment. In one embodiment, the present ALMs comprise a phenotype that exhibits properties of a single polarization phenotype, namely, an M1 polarization phenotype that is proinflammatory in nature, expressing proinflammatory cytokines such as interferon-gamma, interleukin-1α, TNF-alpha, MIP-1a and MCP-1 at an increased level as compared to that in a primary alveolar macrophage population, i.e. expression that is greater than about 20% of the expression level in a primary alveolar macrophage population. The provision of such a stable homogeneous ALM population advantageously permits their use to achieve a known result (e.g. induction of a degree of inflammation due to the expression of proinflammatory cytokines) with a certainty that is not possible with a naturally occurring population of primary alveolar macrophages since these comprise a heterogeneous mixture of phenotypes, including unpolarized phenotype (M0), polarized proinflammatory phenotype (M1) and a polarized anti-inflammatory phenotype (M2).

In another aspect, a kit for use to generate hemangioblasts from PSCs, including a first serum-free differentiation medium for differentiation of the PSCs into hemangioblasts comprising BMP4, VEGF, SCF and a ROCK inhibitor, and a second serum-free differentiation medium comprising at least granulocyte-macrophage colony stimulating factor (GM-CSF), macrophage colony stimulating factor (M-CSF) and interleukin-3 (IL-3) is provided. The amounts of growth factor in the first differentiation medium are generally as follows: an amount of BMP4 of no more than about 100 ng/ml, preferably in the range of about 0.1-100 ng/ml, e.g. 25-75 ng/ml, such as 50 ng/ml, an amount of VEGF of no more than about 100 ng/ml, and preferably in the range of about 0.1-100 ng/ml, e.g. 25-75 ng/ml, such as 50 ng/ml, and an amount of SCF of no more than about 50 ng/ml, and preferably in the range of about 0.1-50 ng/ml such as 10-40 ng/ml, e.g. 20 ng/ml. The medium may also include a ROCK inhibitor in an amount in the range of 0-1 mM. The second differentiation medium includes GM-CSF in an amount of no more than about 100 ng/ml, for example, in the range of about 0.1-100 ng/ml or 25 to about 75 ng/ml, such as 50 ng/ml; M-CSF in an amount of no more than about 50 ng/ml, for example, in the range of about 0.5-50 ng/ml, such as 10-40 ng/ml, e.g. 25 ng/ml; and IL-3 in an amount of up to about 50 ng/ml, for example in the range of about 0.5-50 ng/ml, such as 10-40 ng/ml, e.g. 25 ng/ml.

The kit may further include materials useful to conduct the present method including culture plates, welled plates, petri dishes and the like. The kit may also include instructions for conducting the present method as described herein.

Non-limiting embodiments are described by reference to the following examples which are not to be construed as limiting.

Example 1

Cells

This protocol can be performed on multiple human ESC or iPS cell lines. Human CA1 H1TK (Dr. Andras Nagy, Lunenfeld Research Institute, Toronto, Canada) and H1 (WiCell Research Institute Inc., Madison, USA) ESC lines and cord blood derived iPS cells (NCRM1-NIH Center for Regenerative Medicine, Bethesda, USA; CB-IPSC (Dr. Ian Rogers, Lunenfeld Research Institute, Toronto, Canada)) were used in these experiments.

Media and Growth Factor Supplements

The following media and growth factor supplements were used:
mTeSR™1 culture medium (StemCell Technologies, cat #85850) or mTeSR™ Plus culture medium (StemCell Technologies, cat #05825)
NutriStem® hPSC XF medium (Biological Industries, cat #05-100-1A)
DMEM/F12 (Gibco™, Thermo Fisher Scientific, cat #11320-033)
StemPro™-34 SFM (×1) (Gibco™, Thermo Fisher Scientific, cat #10639011)
Bone morphogenic protein-4 (BMP4) (R&D systems, cat #314-BP-010/CF)
Vascular endothelial growth factor (VEGF) (R&D systems, cat #293-VE-010/CF)
Stem cell factor (SCF) (R&D systems, cat #255-SC-010/CF)
Granulocyte-macrophage colony stimulating factor (GM-CSF) (R&D systems, cat #215-GM-010/CF)
Macrophage colony stimulating factor (M-CSF) (R&D systems, cat #216-MC-010/CF)
Interleukin 3 (IL-3) (R&D systems, cat #203-IL-010/CF)
GlutaMAX™ supplement (Gibco™, Thermo Fisher Scientific, cat #35050061)
L-Ascorbic acid (Sigma-Aldrich, cat #A4403)
Monothioglycerol (MTG) (Sigma-Aldrich, cat #M6145)
Corning® Matrigel® growth factor reduced basement membrane matrix (Corning, cat #354230)

Antibodies

The following antibodies were used:
Fc receptor binding inhibitor polyclonal antibody (Invitrogen, Thermo Fisher Scientific, cat #14-9161-71)
Anti-human CD235a BV421-conjugated antibody (BD Bioscience, cat #562938)
Anti-human APJ APC-conjugated antibody: (R&D systems, cat #FAB856A)
Anti-human c-kit (CD117) APC-conjugated antibody (BioLegend, cat #313205)
Anti-human CD34 PerCP-eFluor 710-conjugated antibody (Invitrogen, Thermo Fisher Scientific, cat #46-0349-41)
Anti-human CD43 PE-conjugated antibody (BD Bioscience, cat #560199)
Anti-human CD11b APC-conjugated antibody (Invitrogen, Thermo Fisher Scientific, cat #17-0118-41)
Anti-human CD11c PE-conjugated antibody (Invitrogen, Thermo Fisher Scientific, cat #12-0116-41)
Anti-human CD45 eFluor 450-conjugated antibody (Invitrogen, Thermo Fisher Scientific, cat #48-9459-41)
Anti-human CD163 PE-Cy7-conjugated antibody (Invitrogen, Thermo Fisher Scientific, cat #25-1639-41)
Anti-human CD169 APC-conjugated antibody (Invitrogen, Thermo Fisher Scientific, cat #17-1699-42)
Anti-human CD206 eFluor 450-conjugated antibody: Invitrogen, Thermo Fisher Scientific, cat #48-2069-41)
Anti-human SIRP-α(CD172a) PerCP-eFluor 710 conjugated antibody (Invitrogen, Thermo Fisher Scientific, cat #46-1729-41)
Anti-human CD116 BV421-conjugated antibody (BD Bioscience, cat #564045)
Anti-human CD14 APC-conjugated antibody (Invitrogen, Thermo Fisher Scientific, cat #17-0149-41)
Anti-human HLA-DR PB-conjugated antibody (BD Bioscience, cat #307623)
Anti-human CD93 PE-conjugated antibody (Invitrogen, Thermo Fisher Scientific, cat #12-0938-41)
Anti-human 25F9 eFluor 660-conjugated antibody (Invitrogen, Thermo Fisher Scientific, cat #50-0115-41)
Anti-human CD64 SB436-conjugated antibody (Invitrogen, Thermo Fisher Scientific, cat #62-0649-41)
Anti-human CD80 PerCP-eFluor 710-conjugated antibody (Invitrogen, Thermo Fisher Scientific, cat #46-0809-41)
Anti-human CD86 SB436-conjugated antibody (Invitrogen, Thermo Fisher Scientific, cat #62-0869-41)

Enzymes and Other Reagents

The following enzymes and other reagents were used:
ReLeSR™ (StemCell Technologies, cat #05873)
TrypLE™ Express Enzyme (1×), phenol red (Gibco™, Thermo Fisher Scientific, cat #12605028)
Trypsin-EDTA (0.25%), phenol red (Gibco™, Thermo Fisher Scientific, cat #25200056)
Collagenase, Type II, powder (Gibco™, Thermo Fisher Scientific, cat #17101015)
Hank's balanced salt solution (HBSS) (Gibco™, Thermo Fisher Scientific, cat #14175095)
HEPES (Sigma-Aldrich, cat #H4034)
Deoxyribonuclease I (DNAse I) (Worthington Biochemical, cat #LS002004)
Penicillin-Streptomycin (5,000 U/ml) (Gibco™, Thermo Fisher Scientific, cat #15070063)
Fetal bovine serum (FBS) (Gibco™, Thermo Fisher Scientific, cat #12483-020)
Dulbecco's Phosphate Buffered Saline (DBPS) (Gibco™, Thermo Fisher Scientific, cat #14190-144)
Rock inhibitor Y-27632 dihydrochloride (Tocris, cat #1254)
Anti-adherence rinsing solution (StemCell Technologies, cat #07010)
Trypan blue solution, 0.4% (Gibco™, Thermo Fisher Scientific, cat #15250061)

Functional and Bacterial Assay Reagents

The following functional and bacterial assay reagents were used:

- Chemically killed *Staphylococcus aureus* (Life Science Technologies, cat. #S23371)
- Vybrant™ DiD Cell-labelling Solution (Fisher Scientific, cat #V22887)
- DiI-AcLDL (Thermo Fisher, L3484)
- *P. aeruginosa* PAO1pMF230 cultures: *P. aeruginosa* PAO1 containing the plasmid-pMF230 for constitutive expression of eGFP (Nivens et al. J Bacteriol. 2001 February; 183(3):1047-57. PubMed 112088042001) were maintained on tryptic soy or LB agar, or grown in tryptic soy broth (TSB) or LB broth, containing carbenicillin at 300 µg/mL. Planktonic cultures were grown in broth overnight in a shaking incubator (37° C., 200 rpm), pelleted (6000×g, 5 min), washed, and resuspended in phosphate-buffered saline (PBS) prior to contact with macrophage cultures.

Tissue Culture Consumables and Equipment

The following tissue culture consumables and equipment were used:

Consumables:
- AggreWell™ 400 microwell tissue-culture treated plates (StemCell Technologies, cat #34415)
- Falcon® 24-well tissue-culture treated plates (Corning, cat #353047)
- Costar® 6-well tissue-culture treated plates (Corning, cat #3516)
- 37 µm reversible strainer small (StemCell Technologies, cat #27215)
- Falcon 40 µm cell strainers (Corning, cat #352340)
- Falcon 70 µm cell strainers (Corning, cat #352350)
- Falcon 100 µm cell strainers (Corning, cat #352360)
- Parafilm M™ Wrapping film (Fisher Scientific, cat #S37440)
- Conical centrifuge tube, 15 ml (Corning, cat #52097)
- Conical centrifuge tube, 50 ml (Corning, cat #352098)
- Eppendorf™ Snap-Cap Microcentrifuge Safe-Lock™ Tubes (Fisher Scientific, cat #05-402-25)
- p10 pipette tips (Sarstedt cat #70.1130.210)
- p200 pipette tips (Sarstedt cat #70.760.211)
- p1000 pipette tips (Sarstedt cat #70.762.211)
- p1000 wide bore (Axygen, Fisher Scientific, cat #14-222-703)
- Sterological pipette, 5 ml, individually wrapped (Corning, cat #356543)
- Sterological pipette, 10 ml, individually wrapped (Corning, cat #356551)
- Sterological pipette, 25 ml, individually wrapped (Corning, cat #356525)
- Kimwipes, small (VWR, cat #21905-026)
- Vacuum filter, Filtropur V50 500 ml 0.22 µm (Sarstedt, cat #83.1823.001)

Equipment:
- SterilGARD biosafety cabinet (Baker)
- Multi-gas incubator (Sanyo, cat #MCO-18M)
- $CO_2$ incubator (Sanyo, cat #MCO-19A/C)
- Eppendorf™ p10 pipette (Fisher Scientific, cat #13-690-026)
- Eppendorf™ p200 pipette (Fisher Scientific, cat #13-690-028)
- Eppendorf™ p1000 pipette (Fisher Scientific, cat #13-690-032)
- Eppendorf™ Easypet™ 3 pipette controller (Fisher Scientific, cat #12-654-195)
- Refrigerated bench-top centrifuge (Eppendorf, cat #5415R)
- Bench-top centrifuge (Eppendorf, cat #5810R)
- Nikon TS100 Eclipse inverted microscope (Nikon)
- Lab Armor™ bead bath (Fisher Scientific, cat #10-876-006) set at 37° C.
- Integra Vacusafe vacuum pump (Integra, cat #158320)
- Hausser Scientific Bright Line Counting Chamber (Fisher Scientific, cat #02-671-51A)
- Eppendorf ThermoMixer Temperature Control Device (Fisher Scientific, cat #05-412-503)
- Gallios 10/3 flow cytometer with red, blue and violet lasers (Beckman-Coulter, PN 773231AF)
- Leica CTRMIC 6000 confocal microscope with a Hamamatsu C910013 spinning disc camera (Leica Microsystems Inc.)
- Leica DMI 3000B microscope with a Hamamatsu ORCA-HR camera (Leica Microsystems Inc.)
- Leica objectives: 5×/0.12, 20×/0.4 and 40×/0.74 air immersion
- Data was analyzed using the Volocity software suite (Quorum Technologies)

Reagent Set Up

Cells—Before initiating a differentiation, ESCs or iPSCs were maintained in feeder-free culture systems with mTeSR, mTeSR Plus or NutriStem medium on matrigel-coated plates. Cord blood iPSCs were maintained with NutriStem, and all other cell lines were maintained with either mTeSR or mTeSR Plus Human ESCs or iPSCs were used at ~70-80% confluency (~5-7 days after passaging) for differentiation experiments.

Defined mTeSR Medium and mTeSR Plus Medium—Frozen mTeSR or mTeSR Plus supplement was thawed overnight at 4° C. Corresponding basal medium and supplement were combined to make a 500 ml stock. Penicillin-Streptomycin (5 ml) was added to a final concentration of 1% Penicillin-Streptomycin. This medium is to be used within 2 weeks and stored at 4° C.

Defined NutriStem Medium—Frozen NutriStem medium was thawed overnight at 4° C. Penicillin-Streptomycin (5 ml) was added to a final concentration of 1% Penicillin-Streptomycin. This medium is to be used within 2 weeks and stored at 4° C.

Matrigel—The matrigel was thawed by placing the vial on ice overnight at 4° C. Aliquots were placed on ice according to the dilution factor (varies per lot) provided by the manufacturer, and stored at −20° C. until ready for use.

Matrigel-Coated Plates—For each well of a 6-well plate, 10 µl matrigel was mixed in 1 ml DMEM/F12. Matrigel/DMEM/F12 solution (1 ml) was added to each well. Parafilm plates were stored at 4° C. for 1-2 weeks. The plates were warmed in an incubator for 1 hour prior to use.

L-Ascorbic Acid—L-ascorbic acid was dissolved in ice-cold sterile, deionized water to a final concentration of 5 mg/ml (may take half an hour, swirl gently every 10 minutes), divided into 5 ml aliquots and stored at −20° C. until required in SP-34 medium preparation.

StemPro™-34 SFM (×1) Culture Medium—StemPro™-34 nutrient supplement was thawed overnight at 4° C. and thoroughly mixed by gently inverting several times. The entire contents (13 mL) of StemPro™-34 nutrient supplement was added directly to a 500 mL bottle of StemPro™-34 SFM Basal medium along with 5 mL Penicillin-Streptomycin (final concentration 1%), 5 ml GlutaMAX, 5 ml L-ascorbic acid (concentration 5 mg/ml), and 19.5 µl MTG, and then swirled gently to mix. Completed SP-34 media is referred to as SP-34+ media. This media can be stored at 4° C. for up to 2 weeks.

Heated Inactivated FBS—FBS was heated to 56° C. for 30 minutes.

Sort Buffer—The following were combined: 490 ml HBSS, 1.192 g HEPES, and 10 ml heat inactivated FBS, and mixed until HEPES was dissolved. The buffer was filtered using a vacuum filter and stored at 4° C. for 6 months.

BMP4—BMP4 was reconstituted with 4 mM sterile HCl to a final concentration of 100 µg/ml. Working aliquots of 100 µl were prepared, and stored at either 4° C. for 1 month or −20° C. for 6 months (avoid freeze-thaw cycles).

GM-CSF, M-CSF, VEGF, SCF, IL-3—Each were reconstituted with 4 mM sterile DPBS to a final concentration of 100 µg/ml. Working aliquots of 100 µl were prepared, and stored at either 4° C. for 1 month or −20° C. for 6 months (avoid freeze-thaw cycles).

Day 0-2 Differentiation Medium—The medium was prepared within 24 hours before intended use. To SP-34+ media, 50 ng/ml BMP4, 50 ng/ml VEGF, 20 ng/ml SCF and 10 µM Rock inhibitor were added.

Day 2-5 Differentiation Medium—The medium was prepared within 24 hours before intended use. To SP-34+ media, 50 ng/ml BMP4, 50 ng/ml VEGF and 20 ng/ml SCF were added.

Day 5+ Differentiation Medium—To SP-34+ media. 50 ng/ml GM-CSF, 25 ng/ml M-CSF and 25 ng/ml IL-3 were added. Media is stable at 4° C. for up to 2 weeks.

Maintenance of Human ESCs and iPSCs Under Feeder-Free Conditions with mTeSR Medium—Prior to passaging, when colonies were 70-80% confluent, the condition of the colonies was inspected to determine if any spontaneous differentiation occurred. Acceptable cells exhibited round colony morphology (merged colonies were acceptable). If >10% differentiation occurred, new cells were used. The number of matrigel-coated plates required was then determined based on the following: 1) H1 ESCs are usually passed at a ratio of either 1:12 or 1:18 every 5-7 days; 2) CA1 ESCs are usually passed at a ratio of either 1:15 or 1:30 every 5-7 days; and 3) NCRM1 iPSCs are usually passed at a ratio of either 1:15 or 1:30 every 5-7 days; and 4) Cord blood derived iPSCs are usually passed at a ratio between 1:20 to 1:50 every 5-7 days. Matrigel-coated plates were warmed in the incubator for 1 hour, and mTeSR™1 media was allowed to come to room temperature. Supernatant is removed from the well that is to be passaged and ReLeSR (200 µl) was added per well and left for 30 seconds with gentle rocking back and forth to cover well. Excess ReLeSR is aspirated from the well which is then incubated at 37° C. for 5 minutes. During this time, matrigel+DMEM/F12 was aspirated and 1 ml of pre-warmed mTeSR™1 was added to each well. The ReLeSR coated wells were removed from the incubator, and mTeSR™1 (1 ml) was added and triturated gently to remove cells. Triturated hESCs were passaged into new wells at the appropriate ratio (as outlined above) and slowly rocked back and forth and side to side to distribute the cells evenly. The cells were incubated in 5% $O_2$, 5% $CO_2$ at 37° C. The medium was replaced daily, and cells were passaged every 7 days or when they reached 80% confluency.

Differentiation of Human ESCs and iPSCs into Primitive Mesoderm—Differentiation of human ESCs and iPSCs was conducted as follows:

Day 0—SP-34+ media was allowed to come to room temperature. ESCs and iPSCs differentiation and confluency were checked. Cells exhibiting less than <10% differentiation and 70-80% confluency were acceptable. Media was aspirated from the cells and 200 µl ReLeSR was added per well, left for 30 seconds, and then swirled to coat the well as per the manufacturer's instructions. Excess ReLeSR was aspirated and the cells were incubated at 37° C. for 5 minutes. DMEM/F12 (1 ml) was added and triturated to loosen the cells for collection in a 15 ml falcon tube. A second 1 ml of DMEM/F12 was added to wash any remaining cells into the same tube. The cells were counted by adding 10 µl of cells to 10 µl of Trypan blue and then counting on a cytometer. Viability of the cells was checked to confirm at least 70% viability. The cells were centrifuged at 600 rcf for 5 minutes. Cells were collected from the centrifuge and DMEM/F12 was aspirated. The cells were gently resuspended in 1 ml Day 0-2 media, triturated, and then the remaining volume of media was added. The AggreWell™ 400 plate was then prepared by adding 250 µl of anti-adherence rinsing solution and centrifuging at 13000 rcf for 5 minutes. Excess rinsing solution was aspirated without aspirating from individual microwells and 1 ml of DMEM or DMEM/F12 was added to each well to rinse wells, followed by aspiration. ESCs and iPSCs were plated at $8 \times 10^5$ cells per 24-well of an AggreWell™ 400 plate. Thus, cells (1 ml) were added in Day 0-2 media to each microwell. The plate was centrifuged at 100 rcf for 3 minutes. Using a microscope, it was confirmed that the cells settled in the microwells and were not overflowing, but were about 80-90% full. The plate was incubated in 5% $O_2$, 5% $CO_2$ at 37° C.

Day 2—SP-34+ media was allowed to come to room temperature. The media from each well of the plate was aspirated, ensuring that the microwells are undisturbed. Day 2-5 media (1 ml) was added dropwise to the side of the well, and the plate was incubated in 5% $O_2$, 5% $CO_2$ at 37° C. to form embryoid bodies.

Differentiation of Human ESC-Derived Primitive Mesoderm into Hematopoietic Progenitor Cells Day 5—SP-34+ media was allowed to come to room temperature. Embryoid bodies were gently dislodged from the microwells using a p1000 widepore pipette. Media and cells were collected from 1 well and passed through a 37 µm reversible strainer placed on top of 15 ml falcon tube. The well was rinsed with 1 ml DMEM/F12 and passed through the strainer. The strainer was inverted onto a new 24-well tissue culture plate and 2 ml of Day 5-20 media was used to wash embryoid bodies into the new well. This was repeated with remaining wells. The plated cells were then incubated in 5% $O_2$, 5% $CO_2$ at 37° C. Embryoid bodies may also remain in the AggreWell™ 400 plates up until day 7 before being transferred to a standard tissue culture plate.

Day 8—Embryoid bodies, either adhered to the bottom of the plate or floating in culture, were checked for attachment to the bottom of the well. If the layer was confluent, 1:2 were passed with gentle trituration, and then incubated in 21% $O_2$, 5% $CO_2$ at 37° C.

Day 10—Day 5+ media was allowed to warm to 37° C. Media (500 µl) was aspirated from each of the wells gently so as to not disturb the embryoid bodies attached to the bottom of the well, or freely floating in the media, and 500 µl of fresh Day 5+ media was added gently, resulting in a half media change. The wells were incubated in 21% $O_2$, 5% $CO_2$ at 37° C.

Day 15 Onwards—Medium was refreshed every 4-5 days as performed on Day 10.

Derivation, Passaging and Maintenance of Human Alveolar-Like Macrophages

Day 12-20 Onwards—By day 12-25 there was a heterogenous population of cells comprised of attached and free floating embryoid bodies and a population of single cells that have emerged from the embryoid bodies. The cord blood-derived iPS cells begin to produce ALMs from as early as 12 days. For the other cell lines, ALMs begin to emerge from ~Day 20. The single cells within the culture were the differentiated ALMs. The two populations can be isolated using two different techniques: i) Trituration technique which includes gently triturating of cells in the well, and since the single cell alveolar-like macrophages are much less adherent, they generally detach much easier than the embryoid bodies; or ii) Straining technique which includes aggressively triturating cells in the well to collect all of the cells, passing the media through a 40 μm strainer such that the single-cell ALMs will pass through and the embryoid bodies will be caught by the strainer. For any cells that do not dissociate by trituration, they can be passaged by incubating them with pre-warmed TrypLE for 10 minutes at 37° C. This becomes more necessary as the passage number increases. ALMs will need to be passaged at a ratio of 1:2 once they reach 90% confluency.

Timing—Maintenance of human ESCs and iPSCs under feeder-free conditions with mTeSR, mTeSR Plus or NutriStem medium is ~5-7 days. Differentiation of human ESCs into primitive mesoderm is ~5-6 days. Differentiation of human ESC-derived primitive mesoderm into hematopoietic progenitor cells is ~10 days. Derivation of human ALMs is ~12-25 days.

Flow Cytometry Protocols

Setup of Gallios Flow Cytometer—Flow cytometry was completed using a Beckman Coulter Galios 10/3 flow cytometer (PN 773231AF) as described previously (Litvak et al. Am J Respir Crit Care Med. 2016; 193(11):1219-29). Briefly, this flow cytometer has 3 solid-state, software controlled lasers (as described in the manufacturers manual): 1) A 22 mW, 488 nm blue laser that controls 5 channels with emission filters at the following wavelengths (in nm): 525 (BP40); 575 (BP30); 620 (BP30); 695 (BP30); and 775 (LP); 2) A 25 mW, 638 nm diode laser that controls 3 channels with emission filters at the following wavelengths (in nm): 660 (BP20); 725 (BP20); and 755 (LP); and 3) A 40 mW, 405 nm violet laser that controls 2 channels with emissions filters at the following wavelengths (in nm): 450 (BP50); and 550 (BP40). On this flow cytometer system, voltages are adjusted using software controlled sliderbars. Mathematical compensation is also achieved using a compensation grid and associated graphical sliderbar interface. User defined event populations can be selected by inclusive gating. Per the manufactures instructions for this particular instrument, unstained controls are used to define the boundaries for fluorescence and intensity based gating. This flow cytometer offers a live gating option, which allows users to control the number of events counted within the defined gate during acquisition rather that acquiring an defined event count for the entire sample.

Figure 3:
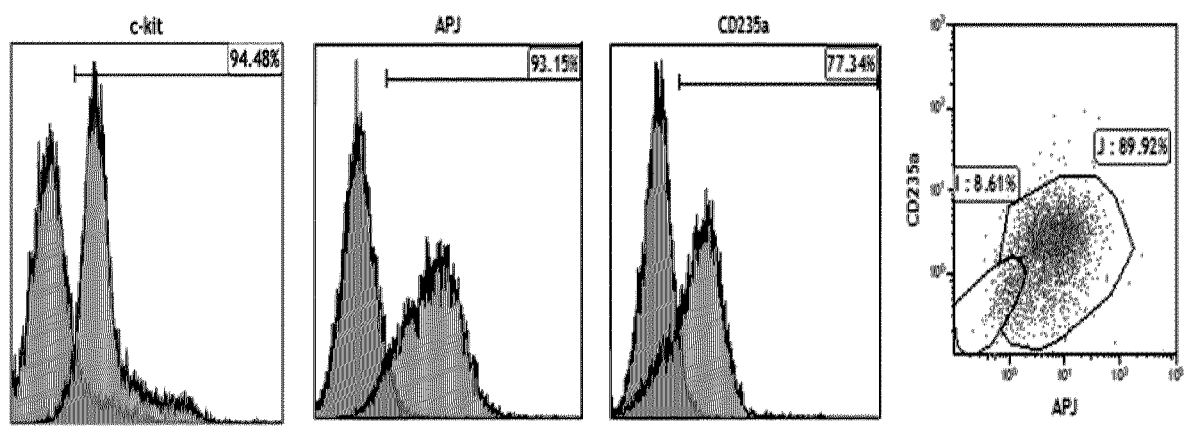
FIG. 3 graphically illustrates expression of primitive mesoderm lineage markers at day 6 of directed differentiation obtained by flow cytometry. The expression of lineage markers presented are from an H1TK differentiation, however they are representative of all ESC (CA1, H1, H1TK) and iPSC (cord blood) lines differentiated. Data are based on n=5 experiments. First histograms, unstained controls; second histograms, stained controls.

Day 6: Primitive Mesoderm Induction—0.25% Trypsin-EDTA and collagenase II was warmed to 37° C. Embryoid bodies and media were collected from 1 well of the plate with gentle trituration into a 15 ml falcon tube. The well was washed with 1 ml DMEM/F12 to collect any remaining embryoid bodies. The embryoid/media mix was centrifuged at 600 rcf for 5 minutes. Whilst centrifugation was occurring, 16.6 μl DNAse I was added to 1 ml 0.25% Trypsin-EDTA. The resulting supernatant was aspirated and the DNAse I+trypsin mixture was added to the tube and incubated for 8 minutes at 37° C. on a shaker. DMEM/F12+10% heat inactivated FBS (2 ml) was added to the tube to stop the reaction, and the tube was centrifuged at 600 rcf for 5 minutes. The resulting supernatant was aspirated and 1 ml of collagenase II was added to the tube which was then incubated for 1 hour at 37° C. on a shaker. DMEM/F12+10% heat inactivated FBS (2 ml) was added to the tube to stop the reaction, and the tube was centrifuged at 600 rcf for 5 minutes. The supernatant was aspirated and 1 ml of sort buffer was added to the tube and the mixture was triturated to resuspend cells. A 40 μm strainer was wetted with sort buffer and placed on top of a 50 ml falcon tube in ice and embryoid cells were pipetted onto the filter. The falcon tube was rinsed with another 1 ml of sort buffer and the rinse was passed through the strainer. Strained cells were collected and divided evenly into 5 eppendorf tubes, labelled as negative, c-kit, CD235a, AJP and CD235a+APJ. The tubes were centrifuged at 1000 rcf for 5 minutes, supernatant was aspirated and the tube was placed on ice. Sort buffer and antibodies were added as follows: Tube 1: negative 100 μl sort buffer; Tube 2: 5 μl c-kit antibody+100 μl sort buffer; Tube 3: μl CD235a antibody+100 μl sort buffer; 1 μl CD235a antibody+100 μl sort buffer; Tube 4: 10 μl APJ antibody+100 μl sort buffer; and Tube 5: 1 μl CD235a antibody+10 μl APJ antibody+100 μl sort buffer. The tubes were incubated on ice in the dark for 30 minutes, 1 ml of sort buffer was added to each tube, and the tube was centrifuged at 1000 rcf for 5 minutes. The supernatant was aspirated and the tube was placed on ice. Sort buffer (300 μl) was added to each tube. Flow cytometry was performed and confirmed the presence of the lineage markers c-kit, APJ and CD235a. An APJ+ CD235a+ population is indicative of primitive mesoderm induction (FIG. 3).

Day 10-20: Hematopoietic Progenitors—Trypsin-EDTA (0.25%) and collagenase II were warmed to 37° C. Embryoid bodies and media were collected from 1 well of the plate with gentle trituration into a 15 ml falcon tube. The well was washed with 1 ml DMEM/F12 to collect any remaining embryoid bodies. Alternatively, if a pure population of the single CD34+CD43+ cells is desired, these may be collected with either gentle trituration (embryoid bodies should stay attached) or pass cells through a 100 μl strainer immediately after collection. The cell/media mix was centrifuged at 600 rcf for 5 minutes. Whilst centrifugation was occurring, 16.6 μl DNAse I was added to 1 ml 0.25% Trypsin-EDTA. Following centrifugation, the supernatant was aspirated and the DNAse I+trypsin mixture was added to the tube and incubated for 8 minutes at 37° C. on a shaker. DMEM/F12+10% heat inactivated FBS (2 ml) was added to the tube to stop the reaction, and the tube was centrifuged at 600 rcf for 5 minutes. The resulting supernatant was aspirated and 1 ml of collagenase II was added to the tube which was then incubated for 1 hour at 37° C. on a shaker. DMEM/F12+10% heat inactivated FBS (2 ml) was added to the tube to stop the reaction, and the tube was centrifuged at 600 rcf for 5 minutes. The supernatant was aspirated and 1 ml of sort buffer was added to the tube and the mixture was triturated to resuspend cells. A 40 μm strainer was wetted with sort buffer and placed on top of a 50 ml falcon tube in ice and the cells were pipetted onto the filter. The falcon tube was rinsed with another 1 ml of sort buffer and the rinse was passed through the strainer. Strained cells were collected and divided evenly into 4 eppendorf tubes, labelled as negative, CD34, CD43 and CD34+CD43. The tubes were centrifuged at 1000 rcf for 5 minutes, supernatant was aspirated and the tubes were placed on ice. The cells were then Fc blocked by adding 1 μl Fc block+50 μl sort buffer to each tube, and then each were incubated on ice in the dark for 5 minutes. Sort buffer and antibodies were added as follows: Tube 1: negative 50 µl sort buffer; Tube 2: 5 µl CD34 antibody+50 µl sort buffer; Tube 3: 10 µl CD43 antibody+50 µl sort buffer; and Tube 4: 5 µl CD34 antibody+10 µl CD43 antibody+50 µl sort buffer. The tubes were incubated on ice in the dark for 30 minutes, 1 ml of sort buffer was added to each tube, and the tube was centrifuged at 1000 rcf for 5 minutes. The supernatant was aspirated and the tube was placed on ice. Sort buffer (300 µl) was added to each tube.

Figure 4:
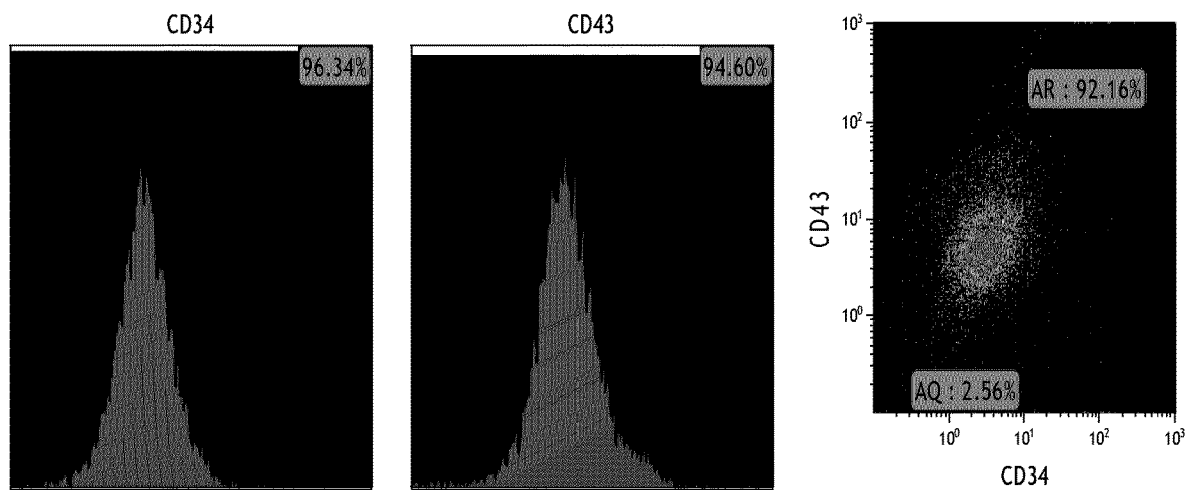
FIG. 4 graphically illustrates expression of hematopoietic progenitor lineage markers at day 10-15 of directed differentiation obtained by flow cytometry. The expression of lineage markers presented are from an H1TK differentiation, however they are representative of all ESC (CA1, H1, H1-TK) and iPSC (cord blood) lines differentiated. Data are based on n=5 experiments. First histograms, unstained controls; second histograms, stained controls.

Flow cytometry was performed and the presence of lineage markers CD34 and CD43 was confirmed. A CD34+ CD43+ population is indicative of hematopoietic progenitor induction (FIG. 4).

Day 12-20: Early Alveolar-Like Macrophages—The early macrophages were single cells that were either attached or floating. Gentle trituration dissociated the cells which were collected and centrifuged at 600 rcf for 5 minutes. The supernatant was aspirated from the cells. 1 ml of sort buffer was added to the cells and triturated to resuspend cells. A 40 µm strainer was wetted with sort buffer, placed on top of a 50 ml falcon tube in ice and cells were pipetted onto the filter. The falcon tube was rinsed with another 1 ml of sort buffer which was passed through the strainer. The strained cells were divided evenly into 9 eppendorf tubes, labelled as negative, single strains: CD11b, CD11c, CD45, CD163, CD169, CD206 and triple strains: CD11b+CD11c+CD45 and CD163+CD169+CD206. Each were centrifuged at 1000 rcf for 5 minutes, supernatant aspirated and tubes put on ice. The cells were Fc blocked as described above, and then incubated on ice in the dark for 5 minutes. Sort buffer and antibodies were added as follows: Tube 1: negative 50 µl sort buffer; Tube 2: 1 µl CD11b antibody+50 µl sort buffer; Tube 3: 5 µl CD11c antibody+50 µl sort buffer; Tube 4: 1 µl CD45 antibody+50 µl sort buffer; Tube 5: 1 µl CD163 antibody+50 µl sort buffer; Tube 6: 1 µl CD169 antibody+50 µl sort buffer; Tube 7: 1 µl CD206 antibody+50 µl sort buffer; Tube 8: 1 µl CD11b antibody+5 µl CD11c antibody+1 µl CD45 antibody+50 µl sort buffer; and Tube 9: 1 µl CD163 antibody+5 µl CD169 antibody+1 µl CD206 antibody+50 µl sort buffer. The tubes were incubated on ice in the dark for 30 minutes, 1 ml sort buffer was added to each tube which was centrifuged at 1000 rcf for 5 minutes. Supernatant was aspirated and the tube was placed on ice, 300 µl sort buffer was added to each tube and contents were transferred to an appropriate tube for flow cytometry.

Day 15+: Alveolar-Like Macrophages—Single cells were collected and centrifuged at 600 rcf for 5 minutes. Supernatant was removed, and 1 ml of sort buffer was added to resuspend cells. Cells were strained as previously described and divided evenly into 8 eppendorf tubes, labelled as negative, CD11b+CD11c+CD45, CD163+CD169+CD206, CD115+CD116+CD83, CD14+HLA-DR, CD93+25F9+ CD64, CD80+CD86 and SIRP-α. The tubes were centrifuged at 1000 rcf for 5 minutes, supernatant removed and the tube was placed on ice. Cells were Fc blocked, and then placed on ice in the dark for 5 minutes. Sort buffer and antibodies were added as follows: Tube 1: negative 50 µl sort buffer; Tube 2: 1 µl CD11b antibody+5 µl CD11c antibody+1 µl CD45 antibody+50 µl sort buffer; Tube 3: 1 µl CD163 antibody+1 µl CD169 antibody+1 µl CD206 antibody+50 µl sort buffer; Tube 4: 5 µl CD115 antibody+1 µl CD116 antibody+5 µl CD83 antibody+50 µl sort buffer; Tube 5: 1 µl CD14 antibody+1 µl HLA-DR antibody+50 µl sort buffer; Tube 6: 1 µl CD93 antibody+5 µl 25F9 antibody+5 µl CD64 antibody+50 µl sort buffer; Tube 7: 2 µl CD80 antibody+5 µl CD86 antibody+50 µl sort buffer; and Tube 8: 1 µl SIRPα antibody+50 µl sort buffer. The tubes were incubated on ice in the dark for 30 minutes, sort buffer was added to each tube which were then centrifuged at 1000 rcf for 5 minutes. Supernatant was aspirated and the tube was placed on ice. 300 µl sort buffer was added to each tube and contents were transferred to flow cytometry tube.

Figure 5:
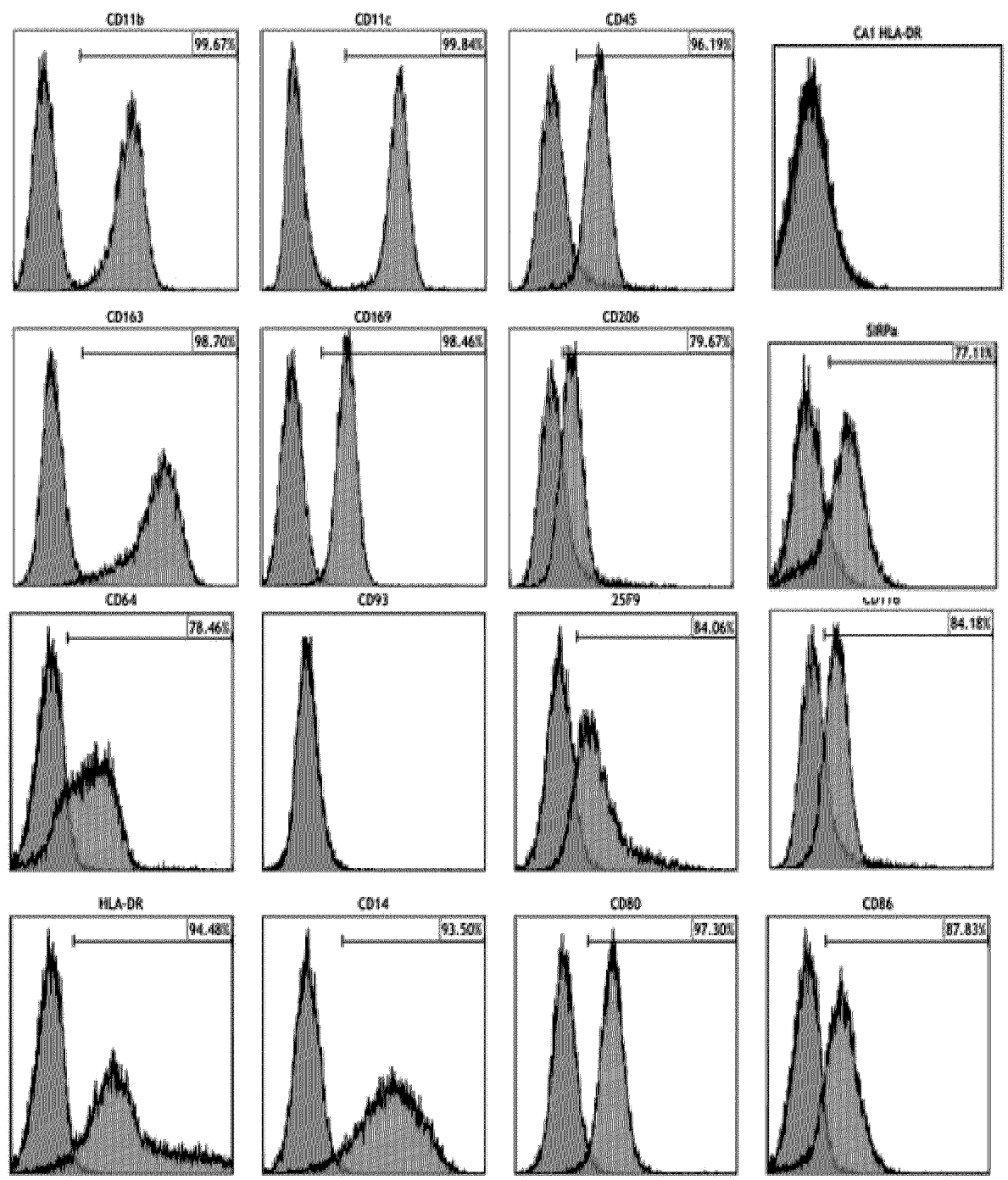
FIG. 5 graphically illustrates expression of alveolar macrophage lineage markers at day 12-25 of directed differentiation obtained by flow cytometry. The expression of majority of the lineage markers are from an H1TK differentiation, however they representative of all ESC (CA1, H1, H1-TK) and iPSC (cord blood) lines differentiated. The only marker that was differentially expressed was HLA-DR. H1TK, H1 and cord blood iPSCs positively expressed HLA-DR, whereas it was negatively expressed in CA1-differentiated ALMs. Data are based on n=5 experiments. First histograms, unstained controls; second histograms, stained controls.

Flow cytometry was performed. ALMs expressed the myeloid lineage markers CD11, CD11c, CD45, AM markers CD163, CD169 and CD206, macrophage markers SIRPα, CD14, CD64 and 25F9, were negative for the monocyte marker CD93, expressed the GM-CSF surface receptor CD116, MHC II HLA-DR, and the T-cell receptor markers CD80 and CD86 (FIG. 5). The homogeneous characteristics of the cells are exemplified well in FIG. 5, where distinct cell populations are described by single peaks for all of the markers tested.

Functional Assessment of ALMs—Prior to functional assessment, ALMs were plated (approximately 60-80% confluency) onto standard tissue culture plates (12 or 24 wells) and incubated with Dil-AcLDL in serum free conditions for up to 4 hours per the manufacturer's instructions. Media was changed to remove the fluorescent dye and ALMs were either imaged immediately using live epifluorescence microscopy or subsequently subjected to a bacterial phagocytosis assay as described previously by Litvack et al., AJRCCM (2016). Briefly, for some experiments live GFP-expressing *Pseudomonas aeruginosa* was co-incubated with ALMs for 45-90 minutes at 37° C. then washed with media or DPBS and fresh media added. For other experiments, cells were stained with Vybrant™ DiD dye for 10 minutes at 37° C. Chemically killed Alexa Fluor 488-fluorescent *Staphylococcus aureus* bacteria was co-incubated with cells overnight at 37° C. Cells were live imaged with a confocal microscope while still in culture.

Plated ALMs were also subjected to a bacterial phagocytosis assay as described above. Briefly, for some experiments live GFP-expressing *Pseudomonas aeruginosa* was co-incubated with ALMs for 45-90 minutes at 37° C. then washed with media or DPBS and fresh media added. For other experiments, chemically killed Alexa Fluor 488 conjugated-*Staphylococcus aureus* bacteria was co-incubated with ALMs for 45-90 minutes (or for some experiments overnight) at 37° C. ALMs showed internalization of live *P. aeruginosa* and *S. aureus*.

Lentiviral Transduction of ALMs—A lentiviral transfer of the murine IL-10 gene using GeneCopoeia's EX-Mm03260-Lv201 lenti-vector to ALMs was conducted as follows. In brief, the vector contained a CMV promoter driving the ORF of mouse IL-10 (Accession: NM_010548.2) followed by SV40-eGFP-IRES-puromycin. To generate the lentivirus, the HIV-based EX-Mm03260-Lv201 lenti-vector, in conjunction with GeneCopoeia's Lenti-Pac™ HIV Expression Packaging vectors were co-transfected into HEK293T cells using GeneCopoeia's EndoFectin™ Lenti Transfection Reagent. Cells were incubated in the presence of 5% $CO_2$ at 37° C. overnight. Growth medium (DMEM+10% FBS) were changed to Opti-MEM containing 3% FBS with the addition of GeneCopoeia's Titerboost™.

Figure 6:
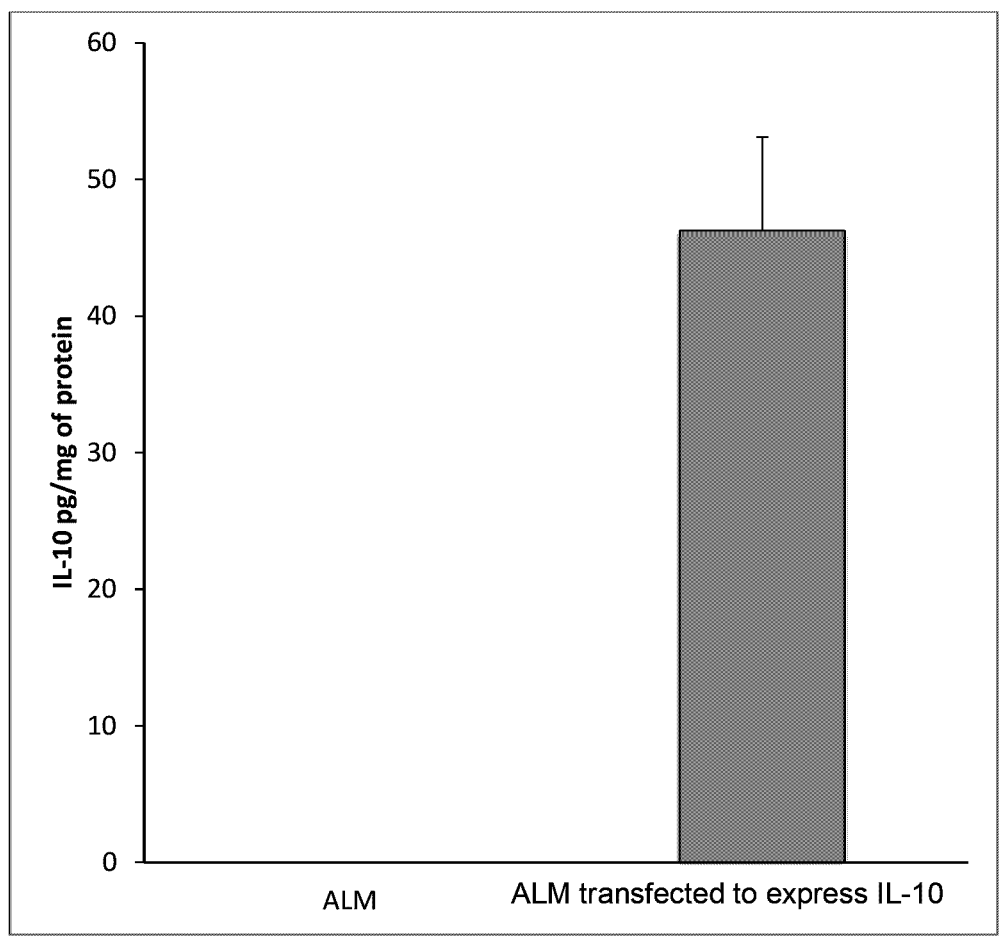
FIG. 6 graphically illustrates transfection of ALMs to successfully express and secrete mouse IL-10.
Figure 7:
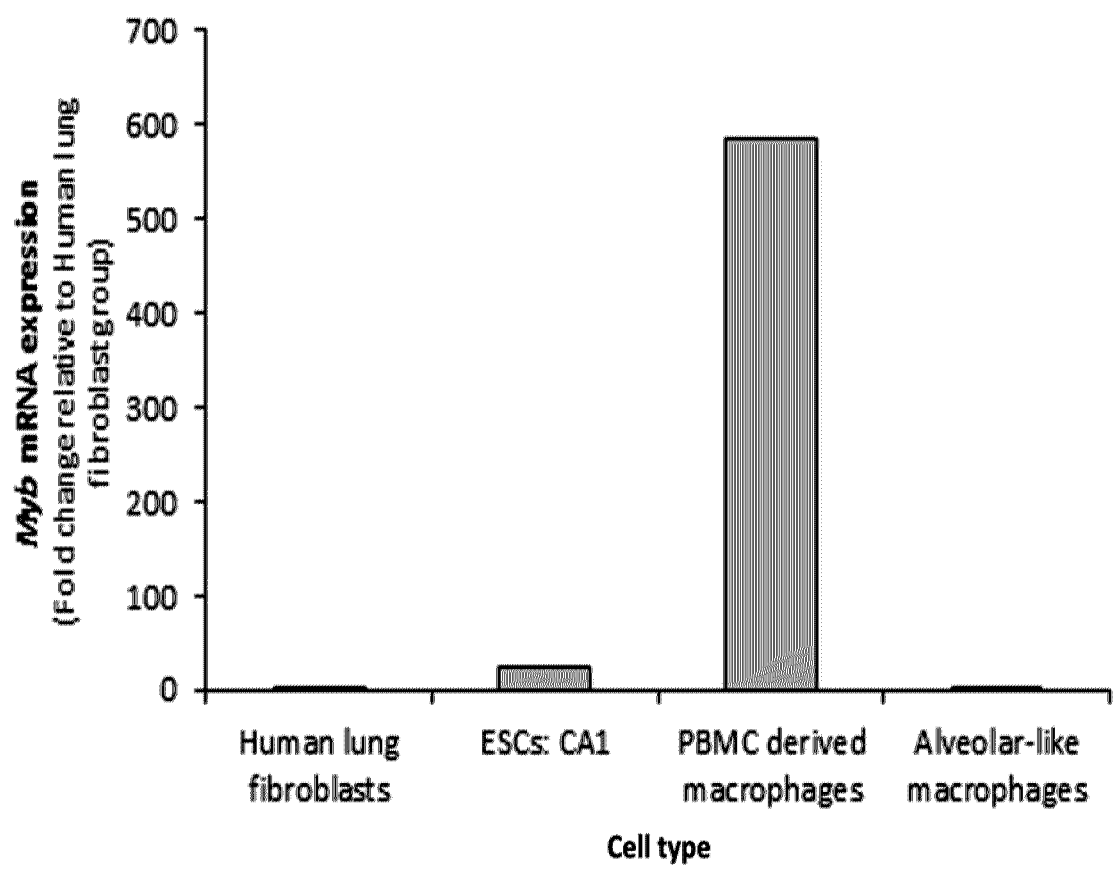
FIG. 7 graphically illustrates the gene expression of Myb in alveolar-like macrophages derived from CA1 ES cells, fibroblasts, CA1 ES cells and peripheral blood mononuclear-derived macrophages obtained by real-time polymerase chain reaction experiments.

Conditioned medium (Opti-MEM+3% FBS) were collected after 24, 48 and 72 hours of incubation. Viral supernatant from transfected packaging cells (i.e., HEK293T cells) was centrifuged at 2000 g for 30 minutes to remove any loose cells and cell debris, and was then transferred to new 15 ml conical tube. PEG 6000 solution was then added to make a final PEG 6000 concentration of 8.5% (v/v) and a final NaCl concentration of 0.3M. The mixture was incubated on ice for 3 to 6 hours, then centrifuged at 2000 g for 30 minutes. The viral particle pellet was resuspended by pipetting in 1/20 of the original harvest volume of Opti-MEM (no serum). Infection of lentivirus was performed on a standard tissue culture 24-well or 6-well plate. Target ALMs were plated at least one day before infection at a cell density about 60-70% confluency. Appropriate amounts of concentrated viral particles were added to the target cells, together with polybrene, to a final concentration of 80 μg/ml. Growth medium were changed one to three days after infection. ALMs were selected under puromycin (0.75 μg/ml) for more than two weeks, positive cells were verified by GFP and IL-10 expression and secretion. ALM transfection was confirmed by visually observing using fluorescent microscopy that some ALMs expressed the GFP reporter. Luminex Cytokine 1-Plex targeting IL-10 was also used. This confirmed that successfully transfected ALMs expressed the IL-10 gene product; whereas cells not undergoing the transfection did not express the IL-10 gene product (FIG. 6).

Figure 2:
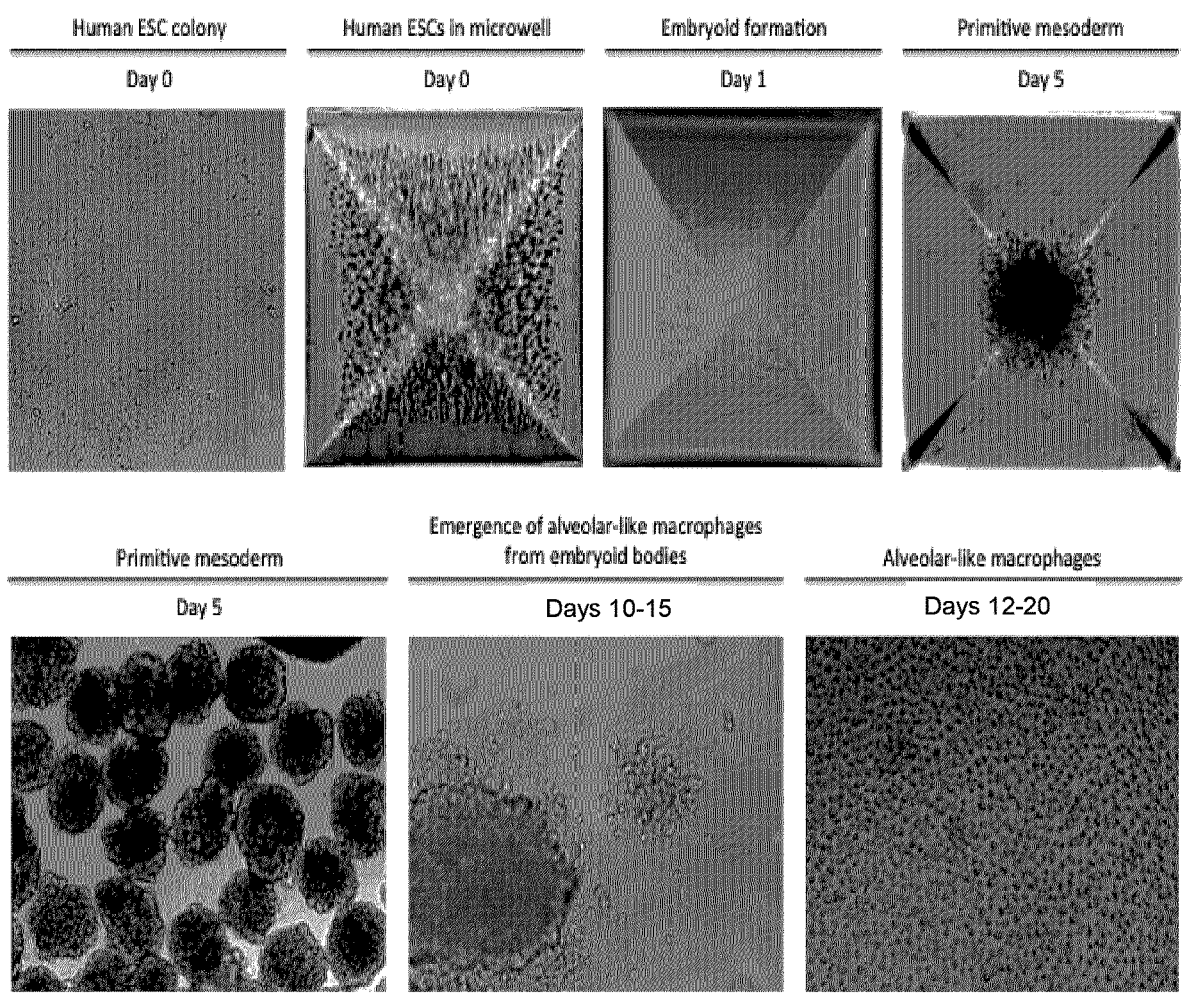
FIG. 2 illustrates morphological changes of human ESCs at different stages of the directed differentiation to alveolar-like macrophages The images are of H1TK cells but are representative of all ESC (CA1, H1, H1TK) and cord blood-derived iPSC lines differentiated. Data are representative of >10 differentiations.

Results—This protocol provides a procedure for the directed differentiation of human ALMs from ESCs and iPSCs for use as a potential cell based therapy (FIG. 1). Representative bright-field images show human ESCs before and after dissociation into microwells on day 0 (commencement of differentiation; single microwell observed), formation of embryoid body on day 1, before and after embryoid bodies are strained and transferred to a standard tissue culture plate on day 5, the emergence of ALMs from an attached embryoid body on day 10-15 and finally a purified population of ALMs on day 12-20 (FIG. 2).

Figure 9:
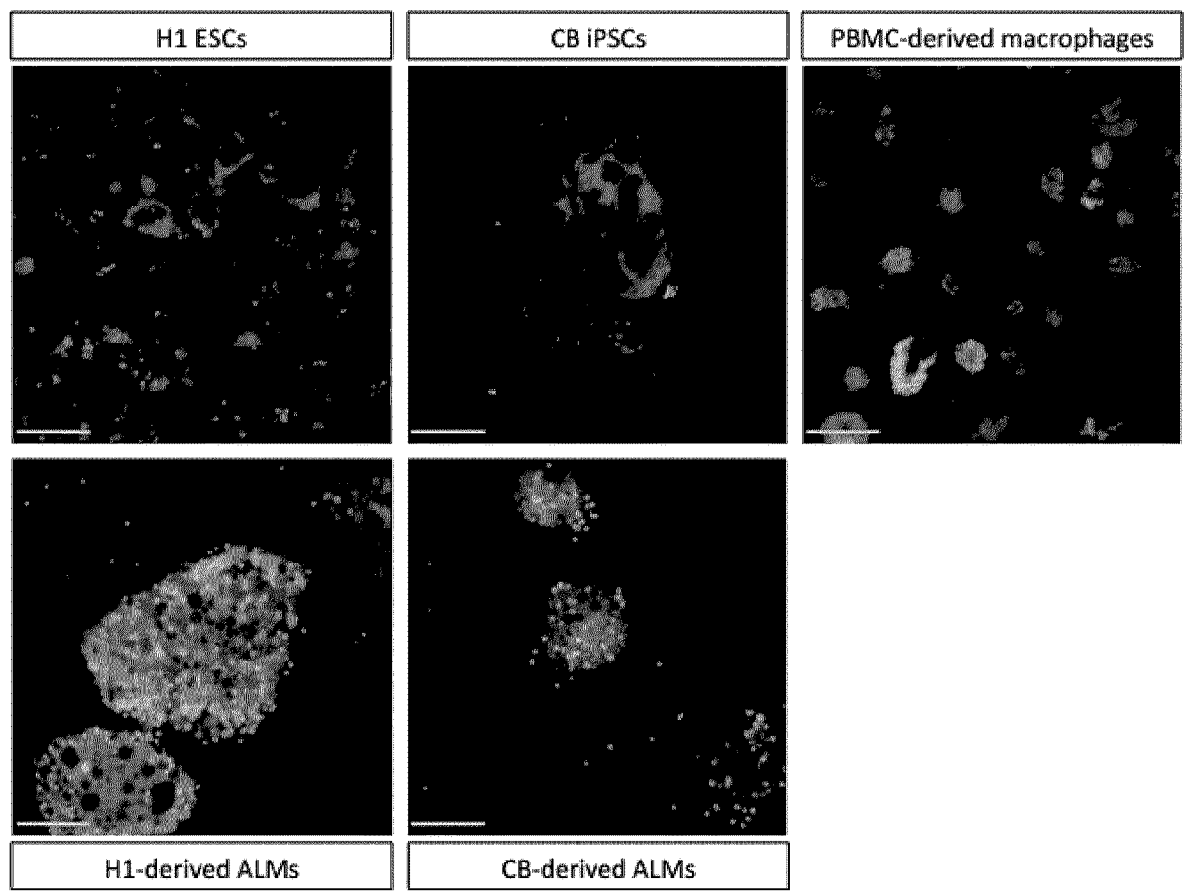
FIG. 9 illustrates the internalization of chemically killed *Staphylococcus aureus* conjugated with Alexa Fluor 488 (shown as bright dots) by H1 ESCs, CB iPSCs, H1 and cord blood (CB) iPSC derived ALMs, and PBMC-derived macrophages overnight. All cells were stained with vibrant DiD dye. Images were taken at ×400 magnification. Scale bar is 25 μm.

With this protocol, human ESCs and iPSCs were first differentiated into primitive mesoderm cells within 5-6 days of induction, followed by the generation of a hematopoietic progenitor population at day 15, and finally induction into ALMs at day 12-25 of the directed differentiation protocol. Primitive mesoderm cells express the lineage markers, c-kit, CD235a and APJ (FIG. 3). The hematopoietic progenitor cells expressed both CD34 and CD43 (FIG. 4). The ALMs expressed numerous cell surface markers (FIG. 5) including myeloid (CD11b, CD11c, CD45) and alveolar macrophage (CD163, CD169, CD206) lineage markers. They expressed the macrophage markers, SIRPα, CD14, CD64 and 25F9, but were negative for the monocyte marker CD93, further indicating that the ALMs were macrophages and not monocytes. In addition, they also expressed cell surface markers responsible for T-cell activation (CD80, CD86), the cell surface receptor for GM-CSF (CD116), H1-derived and cord blood iPSC-derived ALMs express the major histocompatibility complex class II (MHC II) cell surface receptor human leukocyte antigen-DR (HLA-DR), indicating the ALMs could mediate a graft-vs-host response, whereas CA1-derived ALMs did not express HLA-DR. The ALMs also exhibited morphological characteristics of AMs (FIG. 2) and were able to phagocytose chemically killed Alexa Fluor 488 conjugated Staphylococcus aureus bacteria (FIG. 9).

Figure 8:
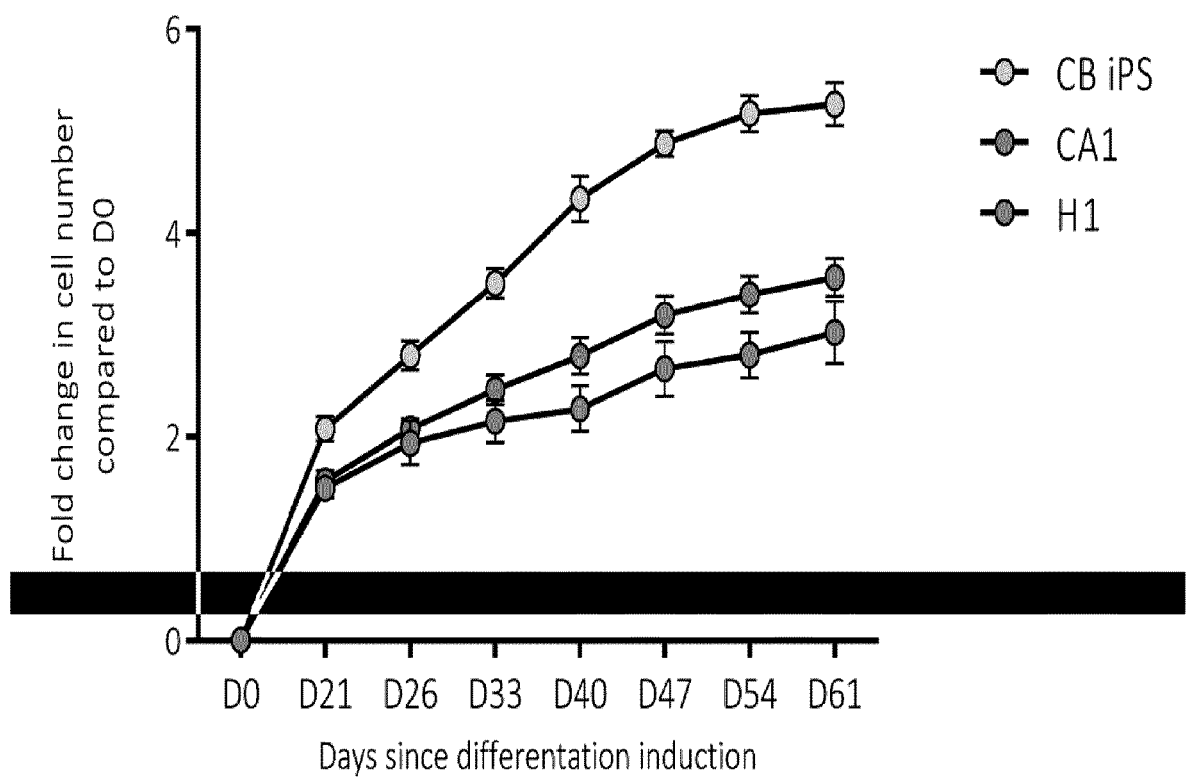
FIG. 8 graphically illustrates the growth rate of cord blood (CB) iPSC derived ALMs (top), CA1 (mid) and H1 (lower) from D0 to D61 of the directed differentiation protocol. Growth rate is expressed as the fold change in cell number compared to D0. The growth rate of each cell line is based on 5 differentiations. Data represented as mean±SEM.

Together, this directed differentiation protocol provides a defined xeno-free method for the derivation of non-naturally occurring ALMs that recapitulates the cell surface markers, morphology and functional capabilities of mature primary AMs. However, unlike naturally occurring AMs, ALMs are able to proliferate in vitro (FIG. 8) and can be maintained in culture for at least six months. Each ESC cell gave rise to approximately 6 ALMs by day 40 of the directed differentiation and at their peak ALMs can have a doubling rate of approximately every 78 hours. ALMs are able to undergo cryopreservation making them an ideal candidate for cell-based therapies in the future. Preliminary results also suggest that ALMs are susceptible to genetic modification and can be transfected to stably express biologics such as IL-10 (FIG. 6) and therefore act as a drug delivery tool. The potential applications for an ALM cell-based therapy are wide, including treating a number of lung diseases for which there are no effective therapies currently available such as bronchopulmonary dysplasia, cystic fibrosis, chronic obstructive pulmonary disease and bacterial and viral pulmonary infections.

The invention claimed is:

1. A feeder-free method of differentiating pluripotent stem cells into hemangioblasts comprising incubating the pluripotent stem cells in a serum-free base medium comprising a first differentiation medium consisting of bone morphogenetic protein 4 (BMP4), vascular endothelial growth factor (VEGF) and stem cell factor (SCF) for a period of time of 1-5 days under hypoxic conditions to yield hemangioblasts or hemangioblast-containing embryoid bodies.

2. The method of claim 1, which is conducted in microwells.

3. The method of claim 1, wherein the hemangioblasts express a hemangioblast mesoderm marker.

4. The method of claim 1, which is conducted under hypoxic conditions of 5% oxygen.

5. The method of claim 1, wherein the differentiation medium consists of BMP4 in an amount in the range of 0.1-100 ng/ml, VEGF in an amount in the range of 0.1-100 ng/ml and SCF in an amount in the range of 0.5-50 ng/ml.

6. The method of claim 1, wherein a ROCK inhibitor is added to the base medium for a period of time.

7. The method of claim 6, wherein the ROCK inhibitor is selective for p160ROCK1.

8. The method of claim 7, wherein the ROCK inhibitor is Y-27632 ((1R,4r)-4-((R)-1-aminoethyl)-N-(pyridin-4-yl)-cyclo-hexanecarboxamide).

9. The method of claim 6, wherein the period of time of is 1-2 days.

10. A method for differentiating pluripotent stem cells into alveolar-like macrophages comprising:
    i) conducting the method of claim 1 to yield hemangioblasts or embryoid bodies comprising hemangioblasts; and
    ii) culturing the hemangioblasts or embryoid bodies in a second differentiation medium comprising at least granulocyte-macrophage colony stimulating factor (GM-CSF), macrophage colony stimulating factor (M-CSF) and interleukin-3 (IL-3) for a period of time sufficient to generate alveolar-like macrophages.

11. The method of claim 10, wherein the second differentiation medium comprises 0.1-100 ng/ml GM-CSF, 0.5-50 ng/ml M-CSF and 0.5-50 ng/ml IL-3.

12. The method of claim 10, wherein the hemangioblasts are cultured in the second differentiation medium for a period of time in the range of about 7-20 days.

13. The method of claim 10, wherein the second differentiation is conducted under normoxic conditions.

14. The method of claim 3, wherein the hemangioblast mesoderm marker is selected from apelin receptor/angiotensin type II receptor (APJ) and CD235a.

* * * * *